(12) United States Patent
Sann et al.

(10) Patent No.: US 8,033,187 B2
(45) Date of Patent: Oct. 11, 2011

(54) DEVICE AND METHOD FOR TAKING SAMPLES

(75) Inventors: Heiner Sann, Magdeburg (DE); Detlef Franz, Merseburg (DE); Andreas Bock, Magdeburg (DE); Klaus Dieter Stoll, Barleben (DE); Udo Reichl, Burgwedel (DE)

(73) Assignee: Max-Planck-Gessellschaft Zur Forderung der Wissenschafter E.V. (DE)

( * ) Notice: Subject to any disclaimer, the term of this patent is extended or adjusted under 35 U.S.C. 154(b) by 466 days.

(21) Appl. No.: 10/586,006

(22) PCT Filed: Jan. 12, 2005

(86) PCT No.: PCT/EP2005/050115
§ 371 (c)(1),
(2), (4) Date: Dec. 11, 2006

(87) PCT Pub. No.: WO2005/068606
PCT Pub. Date: Jul. 28, 2005

(65) Prior Publication Data
US 2008/0022786 A1    Jan. 31, 2008

(30) Foreign Application Priority Data
Jan. 14, 2004    (DE) .......................... 10 2004 001 916

(51) Int. Cl.
*G01N 1/14* (2006.01)
(52) U.S. Cl. ................. 73/864.11; 73/864.15; 73/863.11
(58) Field of Classification Search .. 73/863.11–863.12, 73/864.11, 864.63, 864.34
See application file for complete search history.

(56) References Cited

U.S. PATENT DOCUMENTS

| | | | | |
|---|---|---|---|---|
| 2,434,723 A | * | 1/1948 | Shook | 73/863.71 |
| 3,120,128 A | * | 2/1964 | Snyder, Jr. | 73/864.35 |
| 3,289,482 A | * | 12/1966 | Grant | 73/864.34 |
| 3,986,401 A | * | 10/1976 | Peterson | 73/864.35 |
| 4,046,011 A | | 9/1977 | Olsen | 73/421 |
| 4,585,060 A | * | 4/1986 | Bernardin et al. | 166/64 |
| 5,245,318 A | * | 9/1993 | Tohge et al. | 340/611 |
| 7,121,347 B2 | * | 10/2006 | Murray et al. | 166/372 |
| 2001/0004449 A1 | | 6/2001 | Suzuki et al. | 422/100 |
| 2002/0172600 A1 | * | 11/2002 | Anderson | 417/118 |
| 2003/0138358 A1 | * | 7/2003 | Eipel et al. | 422/100 |
| 2003/0153068 A1 | | 8/2003 | Beland | 435/287.1 |

FOREIGN PATENT DOCUMENTS

DE    4407439    9/1995

OTHER PUBLICATIONS

Patent Abstracts of Japan, vol. 010, No. 017 (C-324), Jan. 23, 1986 & JP 60 172279 A (Hitachi Seisakusho KK), Sep. 5, 1985 abstract.
Patent Abstracts of Japan, vol. 017, No. 589 (C-1124), Oct. 27, 1993 & JP 05 176752 A (Toyo Eng Corp), Jul. 20, 1993 abstract.

* cited by examiner

*Primary Examiner* — Hezron E Williams
*Assistant Examiner* — Nashmiya Fayyaz
(74) *Attorney, Agent, or Firm* — Ballard Spahr LLP

(57) ABSTRACT

The invention relates to a device and a method for taking liquid or gaseous samples from containers and/or tubes that are filled with a medium, in particular from fermenters, by means of negative pressure, wherein an element which acts as a non-return valve is arranged within a sample probe as an inlet for the sample that is to be taken, and a supply line which is able to convey gas and a discharge line which is able to discharge sample are arranged on a common side of the element.

18 Claims, 3 Drawing Sheets

DEVICE AND METHOD FOR TAKING SAMPLES

CROSS REFERENCE TO RELATED APPLICATIONS

Figure 1:
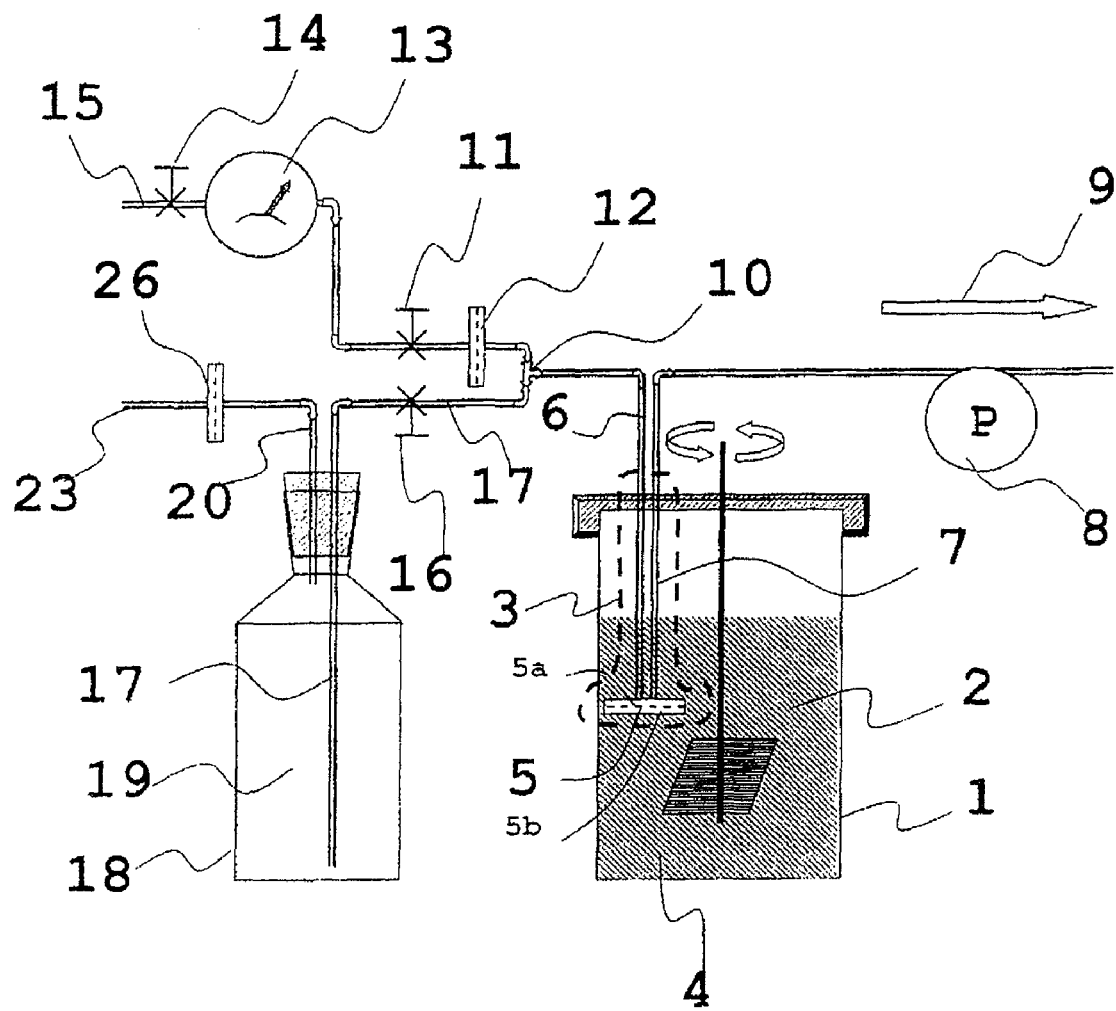

The present application claims priority to German Patent Application No. 10 2004 001 916.9, filed Jan. 14, 2004, which application is incorporated herein fully by this reference.

The invention relates to a device and a method for taking liquid samples from containers and/or tubes that are filled with a medium, in particular from fermenters, by means of negative pressure, wherein an element which acts as a non-return valve is arranged within a sample probe as an inlet for the liquid sample, according to the preambles of claims 1 and 17.

A device for taking samples from a fermenter is known from DE 32 49 399 T1 and U.S. Pat. No. 4,689,306. In order to take the sample, the device has a sampler in the form of a normally closed valve, wherein an annular protrusion is formed on the housing thereof on the side of contact with a sampler, said protrusion being provided to receive an annular groove of a housing of a normally closed valve of the sampler. Between the normally closed valve of the sampler and a holder of the sampler, there is arranged a bacteriological filter which is spaced apart from the normally closed valve of the sampler. This spacing means that, when a sample is taken, a resulting intermediate space within the device also has to be filled with the sample fluid, but is not received in the sampler as sample fluid to be tested. A resulting dead volume of the sample that has been taken means that firstly the sampling cannot be carried out economically in terms of the required sample volume per sample that is taken, and secondly a residual volume from the previous sampling operation is left behind in the device, which due to its properties may lead to falsification of the test results of the next sample that is taken with the desired sterility.

Such sampling devices have a dead volume within the dead space during the sampling operation, which firstly necessitates that a sample be taken with a higher volume and secondly gives rise to the risk of mixing of the residual sample located in the dead volume from the previous sampling operation and the sample substances of the new sampling operation.

Moreover, such devices allow the taking of samples with a fixed volume due to the limited intermediate space. The taking of samples with a larger volume would require a complete changeover of the sampling device.

Furthermore, such sampling devices allow only a certain number of samples to be taken per unit time, since time-intensive interventions are required for this. Most of the conventional sampling devices require the installation of a filter or filter membrane which is intended to ensure the sterility of the sample that is taken. This results in a complicated add-on construction of the devices.

Accordingly, the object of the present invention is to provide a device and a method for taking liquid or gaseous samples from containers and/or tubes that are filled with a medium, by means of negative pressure, in which it is possible to take the sample without any dead volume and under reliably sterile conditions, wherein the device has a simple structure and is cost-effective to manufacture.

This object is achieved in terms of the device by the features of claim 1 and in terms of the method by the features of claim 17.

One essential point of the invention consists in that, in a device for taking liquid or gaseous samples from first containers and/or tubes that are filled with a medium, in particular from fermenters, by means of negative pressure, a supply line which is able to convey gas and a discharge line which is able to discharge sample are arranged in such a way that they are located on the side of an element that is remote from the medium arranged in the first container, said element acting as a non-return valve. The element which acts as a non-return valve forms an inlet for the liquid or gaseous sample and may be arranged within a second container which receives the sample or within a line arrangement between the supply line and the discharge line. In this way, a simple and cost-effective device for sterile sampling is provided, in which automatic opening and closing of the element which acts as a non-return valve is achieved by means of the pressure difference between the first container and the lines of the device, for example within the second container. This is because firstly the element which acts as a non-return valve is opened by means of a negative pressure that is generated in the lines and possibly in the second container, whereupon the sample quantity that is to be taken flows into the discharge line and possibly additionally into the second container. Automatic closing of the element which acts as a non-return valve is then achieved by means of a positive pressure that is generated by a supplied gas within the line arrangement and possibly within the second container. At the same time and thereafter, the sample that is to be taken is completely discharged from the lines and possibly from the second container via the discharge line by means of the positive pressure brought about by the gas. Since the second container is completely isolated from the rest of the medium during the discharge of the gas, it is possible for sampling to be carried out without any dead volume. Sampling without any dead volume can also be achieved if the element is arranged within the line arrangement without the presence of a second container, since the line arrangement is isolated from the rest of the medium during the discharging operation.

Such discharging of the sample with a predefined sample volume, which is regulated for example by means of a pump, out of the line system and possibly the second container of the sampling device at the same time results in reliable emptying of the line system by means of the supplied gas. Since in this way no dead space can be produced within the sampling device in order to form a dead volume, it is possible for the sample to be taken with the desired sample volume that is to be tested, even in the case of small volume quantities, without any additional sample volume being required due to the formation of a dead volume.

Since, after each sample is taken, the line system is completely emptied by means of the gas, which may for example be compressed air, the entire sampling device including the second container is sterile per se before the start of a further sampling operation. Sampling with a high degree of sterility is thus ensured.

Since automatic emptying takes place in a simple and effective manner after the sampling operation, the sampling device according to the invention can be used in an automated manner as a sampling module and allows the connection of detection systems which serve for process monitoring and open-loop/closed-loop control of the sample that has been taken and of the device according to the invention.

Moreover, the time taken for a sampling operation can be kept sufficiently short for online measurements by suitably combining the sample volume to be taken, the conveying speed produced by the pump and the required time period for emptying the line system. This results in a higher number of samples being taken per unit time.

The element may be designed as a non-return valve and due to its arrangement forms a transition point between the medium arranged in the fermenter and the supply and discharge lines arranged at the rear of said element, and thus permits at this interface position a reliable and fast isolation of the sample that has been taken from the rest of the medium, by means of a closure operation.

An integrity test to check the leaktightness of the element which acts as a non-return valve is possible at any point in time. Such a test may be carried out before and after a sampling operation and accordingly makes it possible to increase the operating safety in the container, which may be a bioreactor, in conjunction with the sampling device attached thereto, and makes it possible to improve the handling of the sampling device.

For an additional integrity test, which checks in situ the functioning of the sampling device, the supply line which is able to convey gas is coupled to a first gas-conveying connecting line for joining the supply line to a gas supply connection. Such a coupling is also necessary in order to supply the gas for emptying the line system.

According to one preferred embodiment, a first and second valve are arranged in the region of the first and second end of the first gas-conveying connecting line, so that the connecting line can be shut off at both ends by means of valves.

In addition, a pressure sensor is arranged in the gas-conveying connecting line and a first sterile filter is arranged within the gas-conveying connecting line in the region of the gas supply connection, so that sterile operation of the line system and in particular of the gas-conveying connecting line is ensured and it is possible to check the usually slight positive pressure within the gas line.

According to one preferred embodiment, both the supply line and the discharge line are arranged within the first container and at least partially have a heat-insulating sheathing. This sheathing may be coupled to a heating and/or cooling device for temperature control of the supply and discharge lines, so that heat control and/or cooling of the sample within the sampling probe during the sampling operation is possible in order to extend the validity of the sample that has been taken.

The supply and discharge lines are preferably designed in such a way that they are suitable for supplying and discharging rinsing fluids to and from the element. The rinsing fluids can be fed into the gas-conveying supply line by means of a second connecting line which conveys rinsing fluid, and serve to rinse the entire line system in order to prevent any adhesion and blockage, in particular of the discharge line, by ingredients of the sample substances. The rinsing fluid is a sterile fluid. Following the rinsing operation, the line system is once again emptied by means of gas from the first connecting line at a slight positive pressure. This is preferably a sterile gas. Such a rinsing operation may optionally be carried out between two sampling operations.

Advantageously, a method for taking liquid or gaseous samples from the first containers and/or tubes that are filled with a medium, by means of negative pressure, comprises the following steps:

supplying a gas to the element which acts as a non-return valve on the side of the element that is remote from the medium arranged in the first container, by means of a supply line that can be shut off from other lines by means of at least one valve, discharging the gas from the element which acts as a non-return valve by means of a discharge line and opening a device which is arranged in the discharge line and which acts as a shut-off valve, until the supply and discharge lines are free of sample, closing at least one valve in order to disconnect the supply line from a gas supply connection, generating a negative pressure in the discharge line, for example by means of a pump device, automatically opening the element by means of the negative pressure that has been generated and conveying a sample that is to be taken from the container into the discharge line, supplying a gas which is again supplied at positive pressure, automatically closing the element by means of the positive pressure that has been generated, and conveying the sample out of the discharge line by means of the gas which has again been supplied at positive pressure.

In addition, in order to prevent any blockages and adhesions within the discharge line, the method may comprise the step of supplying rinsing fluid and carrying out the integrity test by supplying gas while shutting off the interior of the device from the surrounding system by means of valves.

Further advantageous embodiments emerge from the dependent claims.

Figure 2:
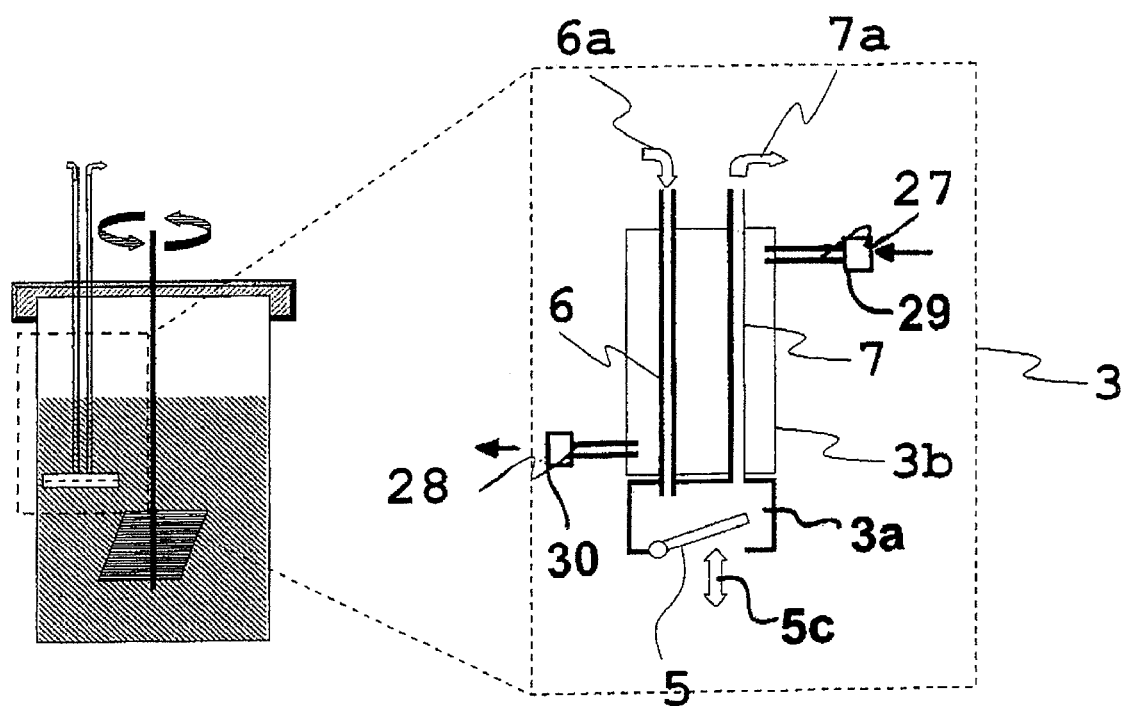
Figure 3:
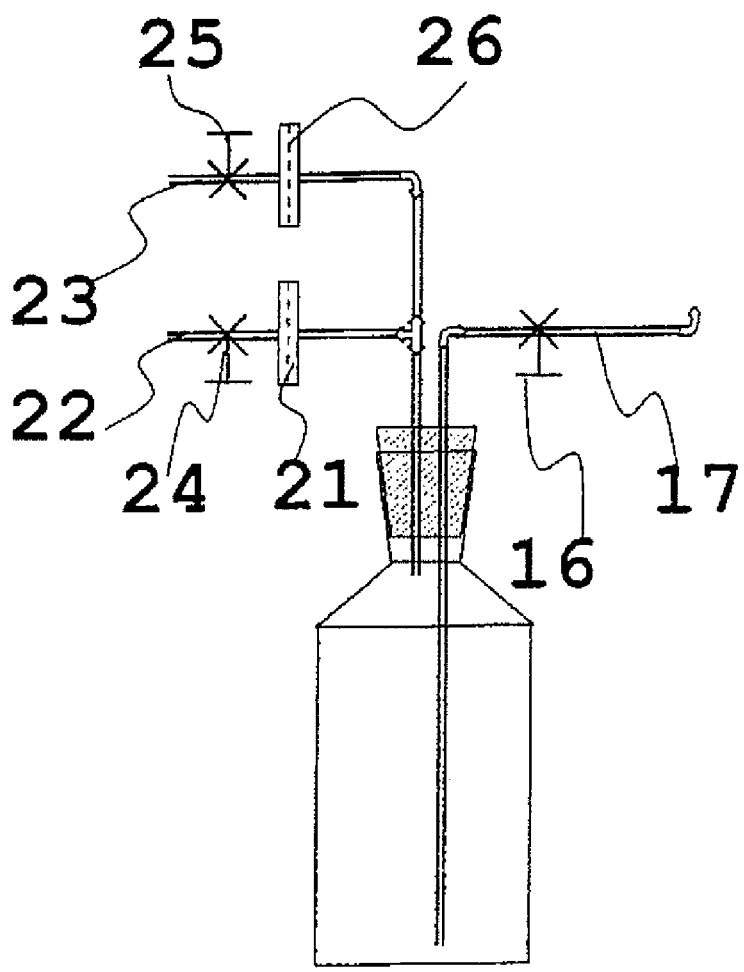

Advantages and expedient features can be found in the following description in conjunction with the drawing, in which:

FIG. 1 shows a schematic diagram of a device according to the invention for taking samples, FIG. 2 shows a schematic diagram of part of the device for taking samples, according to one embodiment of the invention, and FIG. 3 shows a schematic diagram of part of the device for taking samples, according to a second embodiment of the invention.

FIG. 1 shows in a schematic diagram a device according to the invention for taking samples from a first container 1 that is filled with a medium. A sampling probe 3 and a stirrer 4 for stirring the medium 2 are introduced into the medium 2 contained in the container 1. An element 5 which acts as a non-return valve and which is not shown in any great detail in this figure is arranged within the sampling probe 3, said element 5 being made for example of metal or plastic. The element 5 has a sterile rear side 5a and a front side 5b which faces towards the medium, wherein the medium may be designed to be sterile or non-sterile.

A supply line which is able to convey gas and a discharge line 7 which is able to discharge sample are arranged on the rear side 5a of the element 5, that is to say on the sterile side of the element 5 which acts as a non-return valve. A sample which is taken from the medium under the effect of suction by means of the negative pressure of a pump 8, through the non-return valve 5 which forms the inlet to a line arrangement consisting of the supply line and the discharge line, which may be connected to a second container (not shown in this figure), can be discharged into a detector device (not shown here) or a storage container (not shown directly here), as indicated by the arrow 9.

The supply line 6 is connected by means of a T-piece 10 to a first gas-conveying connecting line which is in turn connected to a gas supply connection 15. Via the gas supply connection 15, compressed air is supplied to the supply line 6 for as long as the shut-off valves 11 and 14 are in their open position.

In order to ensure a supply of sterile compressed air, a sterile filter 12 is provided. In addition, the compressed air which is supplied at a slight positive pressure is checked with regard to its pressure by means of a manometer 13.

Connected to the other end of the T-piece 10 is a second connecting line 17 which conveys rinsing fluid and is connected to a container 18 which contains a sufficient amount of rinsing fluid 19, such as distilled water for example. A connecting line 20 for gas and liquid connects the container 18 via a second sterile filter 26 arranged therein to a further gas supply connection 23, in order to provide pressure equalization for the container 18. This gas supply connection 23 can be switched on when necessary.

When a rinsing operation is to be carried out, a valve 16 to the supply line 6 is opened while the valves 11 and 14 of the first gas-conveying connecting line are closed. Once the rinsing fluid has left the supply and discharge lines 6, 7 via the pump 8, and rinsing of the lines 6, 7 and of the rear side 5a of the element 5 has been carried out, the valve 16 is closed and the first and second valves 11, 14 are opened in order to give rise to an emptying operation of the line system comprising the supply and discharge lines 6, 7 by means of the sterile compressed air that is supplied.

FIG. 2 shows, in a schematic diagram, part of the device for taking samples according to one embodiment of the invention. In this diagram, the sampling probe 3 is shown on an enlarged scale. As can be seen from the enlarged representation of the sampling probe, the latter consists of the second container 3a on the underside, the supply line 6 and the discharge line 7, the flow directions of which are indicated by the arrows 6a and 7a, and a sheathing 3b which has a heat-insulating effect. Such a sheathing 3b may additionally be connected to a heating or cooling device 29, 30, by means of supply line 27 and discharge line 28 in order to achieve temperature control or cooling of the samples as they are being taken, in order to extend their validity.

During a sampling operation, the following sequence takes place:

While the first and second valves 11, 14 are closed, the pump 8 generates a negative pressure within the line system, which conveys a sample out of the medium 2 to be tested, through the open element 5 which acts as a non-return valve and firstly into the second container 3a. The negative pressure that is generated is able to bring about automatic opening of the element 5, the opening and closing movement of which is indicated by the arrow 5c.

The desired sample volume of the sample that is to be taken is regulated by means of the pump strength of the pump 8. Once a predefined sample volume with a predefined conveying time has been achieved, compressed air at a slight positive pressure is fed in via the supply line 6, whereupon automatic closure of the element 5 takes place. At the same time, with the valve 16 closed and the valves 11 and 14 open, the sample is conveyed out of the line system comprising the lines 6, 7 by means of the positive pressure of the compressed air, in such a way that said sample is fed into a storage container (not shown here) via the discharge line 7. At the same time, the supplied compressed air reliably brings about emptying of the line system, so that the latter is free of sample and is sterile if sterile compressed air is used.

For an integrity test that can be carried out in order to check the functioning of the sampling device, with the valve 16 closed and the pump 8 not in operation, compressed air is supplied to the line system via the gas supply connection 15 in order to generate a positive pressure. If the element 5 which acts as a non-return valve and which forms a type of sterile barrier to the rest of the medium 2 is leaktight, the positive pressure continues to remain after the valve 14 has been closed. On the other hand, if the pressure drops, this indicates that the element 5 is not leaktight.

FIG. 3 shows, in a schematic diagram, part of the device for taking samples according to the invention. A rinsing fluid supply connection 22 is additionally connected to the container 18 via a part of the line 20 which conveys rinsing fluid and a further sterile filter 21 and a further valve 24 arranged respectively therebetween. The rinsing fluid supply connection 22 serves to refill the container 18 with rinsing fluid. The gas-conveying part of the line 20 additionally has a further valve 25 between the filter 26 and the gas supply connection 23 for the purpose of supplying, discharging or metering gas.

The embodiment of the invention is not limited solely to the example described and the aspects mentioned above; rather, a large number of technical modifications are also possible within the scope of the claims.

LIST OF REFERENCES 1 first container
2 medium
3 sampling probe
3a second container
3b heat-insulating sheathing
4 stirrer
5 element which acts as a non-return valve
5a rear side of the element
5b front side of the element
5c direction of movement of the element
6 supply line
6a flow direction within the supply line
7 discharge line
7a flow direction within the discharge line
8 pump
9 discharge direction
10 T-piece
11, 14, 16, 24, 25 valves
12, 21, 26 sterile filter
13 manometer
25, 23 gas supply connection
17 connecting line which conveys rinsing fluid
18 third container
19 rinsing fluid
20 connecting line for gas and rinsing fluid
22 rinsing fluid supply connection
23 gas supply connection
27 heating or cooling supply line
28 heating or cooling discharge lin
29, 30 heating or cooling device

The invention claimed is:

1. A sample probe for taking liquid samples from a first container that is filled with a liquid medium, wherein a non-return valve element is arranged within the sample probe as an inlet to a second container, the inlet for a liquid sample that is to be taken, which element is opened solely by means of negative pressure, wherein a supply line which is able to convey gas to the second container and one discharge line which is able to discharge sample and to convey the negative pressure for opening the valve element for suction of the sample, are arranged on the side of the element that is remote from the medium arranged in the first container, wherein the supply line which is able to convey gas to close the valve element and the discharge line which is able to discharge sample are in each case connected directly to the second container which receives the sample via the inlet so that the sample inside the second container is completely isolated from the rest of the medium during the conveying of the gas and the sample by closing the valve element.

2. Device according to claim 1, characterized in that the element is arranged within a line between the supply and discharge lines.

3. Device according to claim 1, characterized in that the supply line which is able to convey gas and the discharge line are suitable for supplying and discharging gases at positive pressure to and from the non-return valve element.

4. Device according to claim 3, characterized in that the non-return valve element is designed in such a way that the element can be closed automatically by means of the supply of gas at positive pressure.

5. Device according to claim 1, characterized in that the supply line and the discharge line are arranged within the first container and at least partially have a sheathing for temperature control and/or cooling of the supply line and the discharge line.

6. Device according to claim 5, further comprising a heating device for temperature control or a cooling device for cooling of the supply line and of the discharge line inside the sheathing.

7. Device according to claim 1, characterized in that the supply line which is able to convey gas is connected to a first gas-conveying connecting line for joining the supply line to a gas supply connection.

8. Device according to claim 7, further comprising a first and second valve arranged in the region of a first and second end of the gas-conveying connecting line.

9. Device according to claim 7 further comprising a pressure sensor in the gas-conveying connecting line.

10. Device according to claim 7 further comprising a first sterile filter is arranged in the gas-conveying connecting line.

11. Device according to claim 7, characterized in that the supply and discharge lines are suitable for supplying and discharging rinsing fluids to and from the element.

12. Device according to claim 11, characterized in that the supply line can be connected to a second connecting line which conveys rinsing fluid.

13. Device according to claim 12, characterized in that the second connecting line which conveys rinsing fluid is connected to a third container which contains a rinsing fluid.

14. Device according to claim 11, characterized in that, for the purposes of pressure equalization, a third container is connected to a further gas supply connection via a further gas-conveying connecting line with a further sterile filter arranged therein.

15. Device according to claim 11, characterized in that a third container is additionally connected to a rinsing fluid supply connection via a further connecting line which conveys rinsing fluid with a further sterile filter arranged therein.

16. Method for taking liquid samples from a first container that is filled with a liquid medium, wherein a non-return valve element is arranged within a sample probe as an inlet to a second container, the inlet for a liquid sample that is to be taken, which element is opened solely by means of negative pressure, characterized by the following steps:

supplying a gas to the non-return valve element on the side of the element that is remote from the medium arranged in the first container, by means of a supply line that can be shut off from other lines, discharging the gas from the non-return valve element by means of one discharge line and opening a valve which is arranged in said one discharge line and which acts as a shut-off valve, until the supply line and said one discharge line are free of a sample, closing at least one valve in order to disconnect the supply line from a gas supply connection, generating in said one discharge line a negative pressure with respect to the pressure that exists in the first container, automatically opening the valve element by means of the negative pressure that has been generated and conveying a liquid sample that is to be taken from the first container into said second container and said discharge line, supplying a gas which is again supplied at positive pressure with respect to the pressure that exists in the first container, automatically closing the valve element by means of the positive pressure that has been generated, and conveying the liquid sample out of the discharge line by means of the gas which has again been supplied at positive pressure, wherein the supply line which is able to convey gas and the discharge line which is able to discharge sample are in each case connected directly to the second container which receives the sample so that the sample inside the second container is completely isolated from the rest of the medium during the conveying of the gas and discharging of the sample.

17. Method according to claim 16, characterized in that, in order to prevent any blockages and adhesions within the discharge line that are caused by ingredients of a sample, a rinsing fluid is supplied via the supply line and discharged via the discharge line after the step of conveying the sample out of the discharge line.

18. Method according to claim 17, characterized in that, after the step of supplying and discharging the rinsing fluid, the steps of supplying and discharging the gas are repeated.

* * * * *